United States Patent
Johnson

(12) 
(10) Patent No.: US 9,522,077 B1
(45) Date of Patent: Dec. 20, 2016

(54) ADJUSTABLE DUAL FUNCTION SPINAL EXOSKELETON ACTIVE SPINAL ORTHOSIS

(71) Applicant: Alwyn Patrice Johnson, Englewood, CO (US)

(72) Inventor: Alwyn Patrice Johnson, Englewood, CO (US)

(*) Notice: Subject to any disclaimer, the term of this patent is extended or adjusted under 35 U.S.C. 154(b) by 302 days.

(21) Appl. No.: 13/899,541

(22) Filed: May 21, 2013

Related U.S. Application Data

(60) Provisional application No. 61/649,787, filed on May 21, 2012.

(51) Int. Cl.
*A61F 5/00* (2006.01)
*A61F 5/02* (2006.01)

(52) U.S. Cl.
CPC ...................... *A61F 5/02* (2013.01)

(58) Field of Classification Search
CPC .......... A61F 5/055; A61F 5/012; A61F 5/022; A61F 5/024; A61F 5/34; A61F 5/028; A61F 2002/30187; A61F 2002/30433; A61F 2002/30441; A61F 2002/30563; A61F 2002/30568; A61F 2002/30571; A61F 2002/30574; A61F 2002/30604; A61F 2002/30662; Y10S 128/23

USPC .. 602/17–19; 128/DIG. 19, 95.1, 96.1, 99.1, 128/874–875
See application file for complete search history.

(56) References Cited

U.S. PATENT DOCUMENTS

| | | | | |
|---|---|---|---|---|
| 4,807,605 A * | 2/1989 | Mattingly | ........................ | 602/19 |
| 5,135,471 A * | 8/1992 | Houswerth | ...................... | 602/19 |
| 2004/0133138 A1* | 7/2004 | Modglin | ......................... | 602/21 |
| 2011/0105971 A1* | 5/2011 | Ingimundarson et al. | ..... | 602/19 |

* cited by examiner

*Primary Examiner* — Michael Brown
(74) *Attorney, Agent, or Firm* — Oppedahl Patent Law Firm LLC; Aileen Law

(57) ABSTRACT

A spinal orthosis is provided that includes a cervical section, a lumbar section, a thoracic section and a tensioner. The cervical section has one or more pads configured for placement at a clavicle of a wearer. The lumbar section is connected to the cervical section and has an abdominal Para-umbilical buttress configured for an anterior region of a lumbar spine. The buttress is further configured to provide compression and gripping of the spine. The lumbar section includes one or more digits with a gripping portion at around ribs and/or iliac crest of the wearer. The thoracic section is connected to the cervical section. The tensioner connects the lumbar section to the thoracic section.

18 Claims, 16 Drawing Sheets

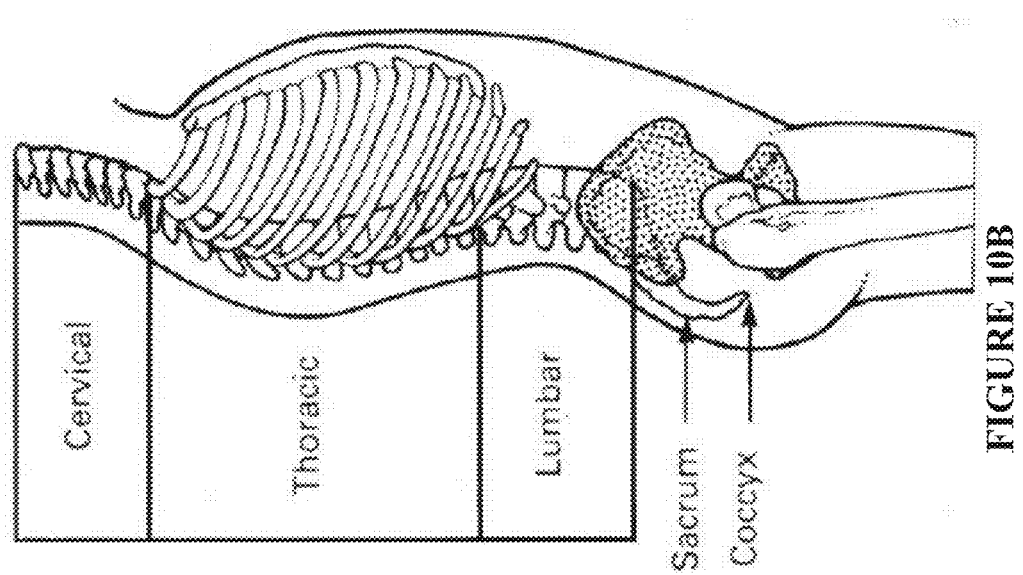

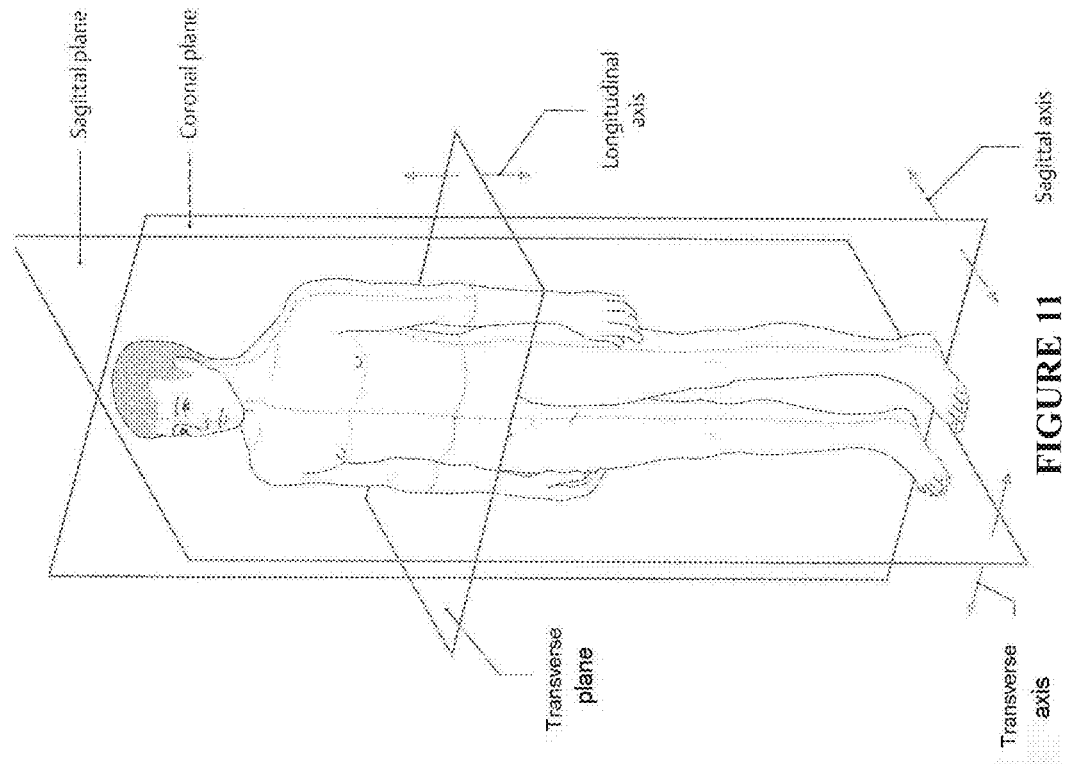

ADJUSTABLE DUAL FUNCTION SPINAL EXOSKELETON ACTIVE SPINAL ORTHOSIS

CROSS-REFERENCE TO RELATED APPLICATION

This application claims priority under 35 U.S.C. 119(e) to U.S. Patent Application No. 61/649,787, filed on May 21, 2012. The entire disclosure of U.S. Patent Application No. 61/649,787 is hereby incorporated herein by reference.

FIELD OF THE INVENTION

The present invention generally relates broadly to an exoskeleton. More specifically, the present invention relates to an exoskeleton orthosis for stabilization and action-assistance of the torso or spine.

BACKGROUND INFORMATION

There are presently many spinal brace devices, postural support garments and wearable devices that aid the movement and transportation of infirmed persons. Presently, these devices are generally categorized as spinal orthoses. Some orthoses are custom made, in a standard manufacturing process where a cast is made of the wearers' trunks. An orthosis is then molded from this casting. This process is time consuming and costly. Spinal orthoses are used to treat a variety of skeletal conditions associated with the skeletal structure, including osteoporosis, spinal deformities, injury and osteoporosis by applying tensile and compressive forces to selected anatomy along the wearer's spine, abdomen, chest and torso. Spinal orthoses include Cervical Orthoses, thoracic lumbar sacral orthosis, and cervical thoracic lumbar sacral orthosis. These orthosis are designed to provide support and immobilization of the spinal regions that they enclose. There are different types of spinal orthoses typically categorized by the vertebral level intended for treatment. Many persons who are of lower income are deprived of the benefit of such orthoses because of the high cost. Persons who do have access to orthoses chose not to participate in many sporting or rehabilitative activities, which may improve their health, because of the high rigidity of the current orthoses. The rigidity prevents freedom of movement of the spine to comfortably and efficiently perform demanding and simple physical activities including transition from standing to seating.

Paraplegics, children born with spinal irregularities, the aging and persons with back injuries have a need for postural support and stabilization devices that allow them to participate in basic activities for daily living. Persons who perform physically strenuous and intensive activities due to their occupations and/or for recreational activities also need devices that transfer load away from the spine and provide truncal stability and support to prevent injury to the torso from occurring. Individuals who must remain seated for extended periods of time often develop back strain or pain. Proper posture support for these individuals can aid in relief of this strain. The development of a flexible spinal device that prevents back injury and assists in providing core stability to the trunk is currently very limited. There are many factors that contribute to back injury, such as overloading, twisting and jerking.

As yet, very little development has taken place in the area of spinal exoskeletons and active spinal orthoses intended to reduce pain of an infirmed person, rehabilitate an individual and prevent back injury from occurring during strenuous activities. There is a need to provide a spinal orthosis that is adjustable to fit persons of different sizes, provides an adjustable fit for a wearer over time, and yet provides superior ability for the device to function as an active orthosis. There is a need to provide a spinal orthosis that is relatively inexpensive, yet provides a comfortable and durable solution for the wearer. There is also a need for the orthosis to be non-obtrusive and wearable as an undergarment by a user.

SUMMARY OF THE INVENTION

A spinal orthosis is provided that includes a cervical section, a lumbar section, a thoracic section and a tensioner. The cervical section has one or more pads configured for placement at a clavicle of a wearer. The lumbar section is connected to the cervical section and has an abdominal Para-umbilical buttress configured for an anterior region of a lumbar spine. The buttress is further configured to provide compression and gripping of the spine. The lumbar section includes one or more digits with a gripping portion at around ribs and/or iliac crest of the wearer. The thoracic section is connected to the cervical section. The tensioner connects the lumbar section to the thoracic section.

BRIEF DESCRIPTION OF THE DRAWINGS

Referring now to the attached drawings which form a part of this original disclosure:

FIG. 10B: Segments of Human Spine
FIG. 11: Cardinal Planes and Axes in the human body

DETAILED DESCRIPTION OF THE PREFERRED EMBODIMENTS

Figure 1A:
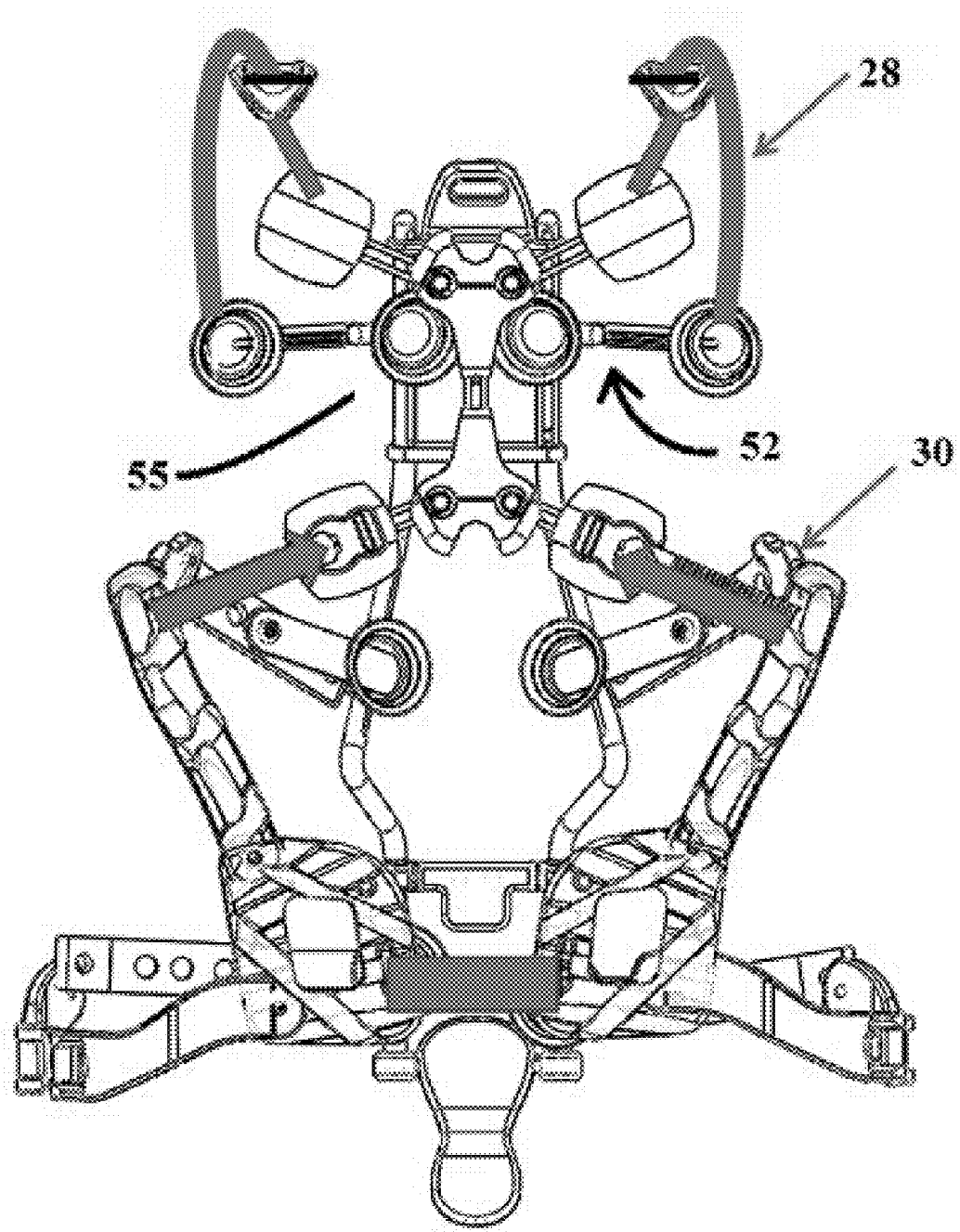
FIG. 1A is the front view of the Dual Function Adjustable Spinal Exoskeleton—Active Spinal Orthosis, showing the shoulder strap 1, which is connected to the sternal-clavicular crest 2, the Chondral digit web 3, and the distal chondral digit 4, the abdominal Para-umbilical buttress or sheath 5, and the Pelvic plate 6.
Figure 1B:
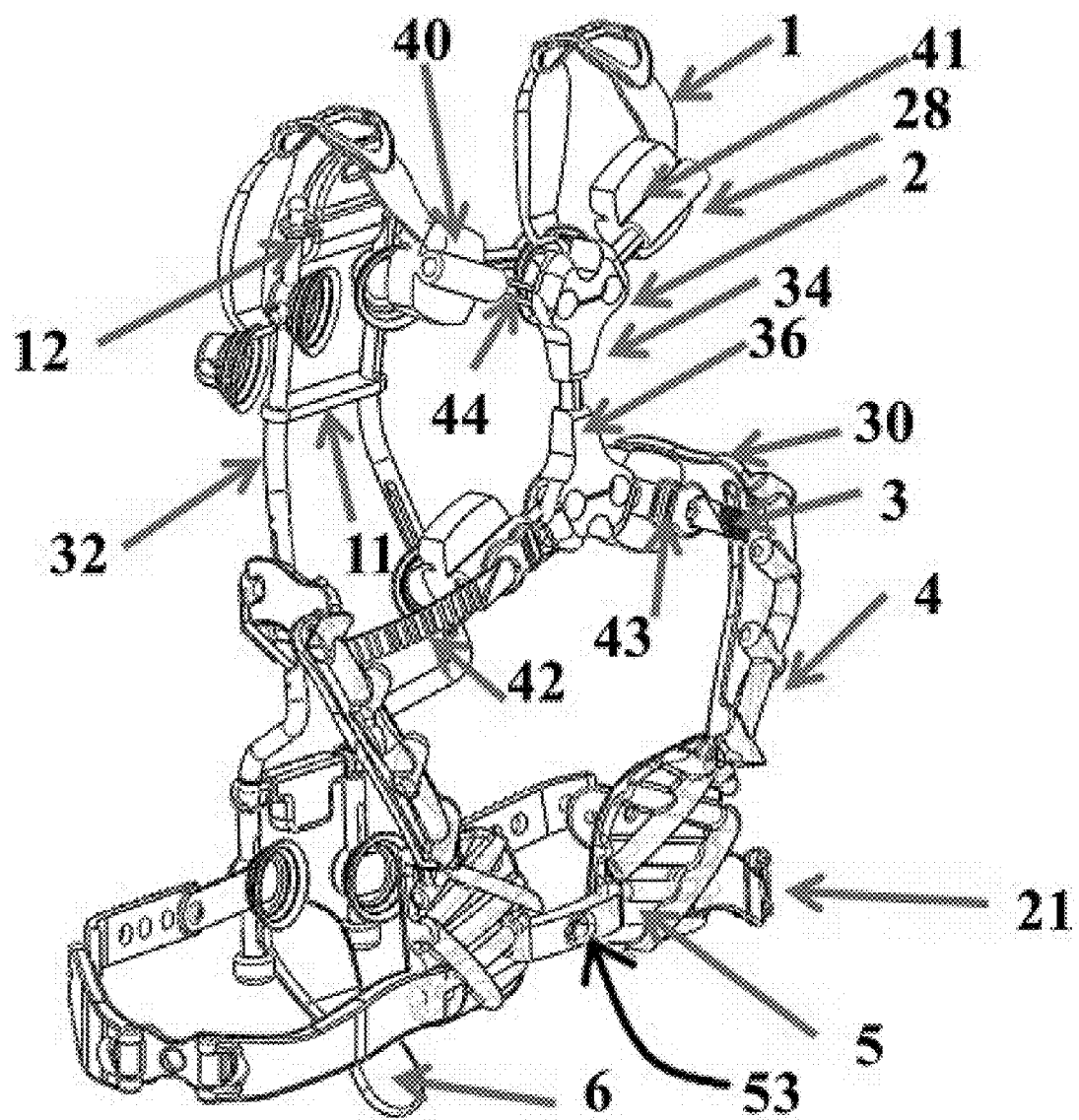
FIG. 1B is a side perspective view of the orthosis of FIG. 1A.
Figure 2:
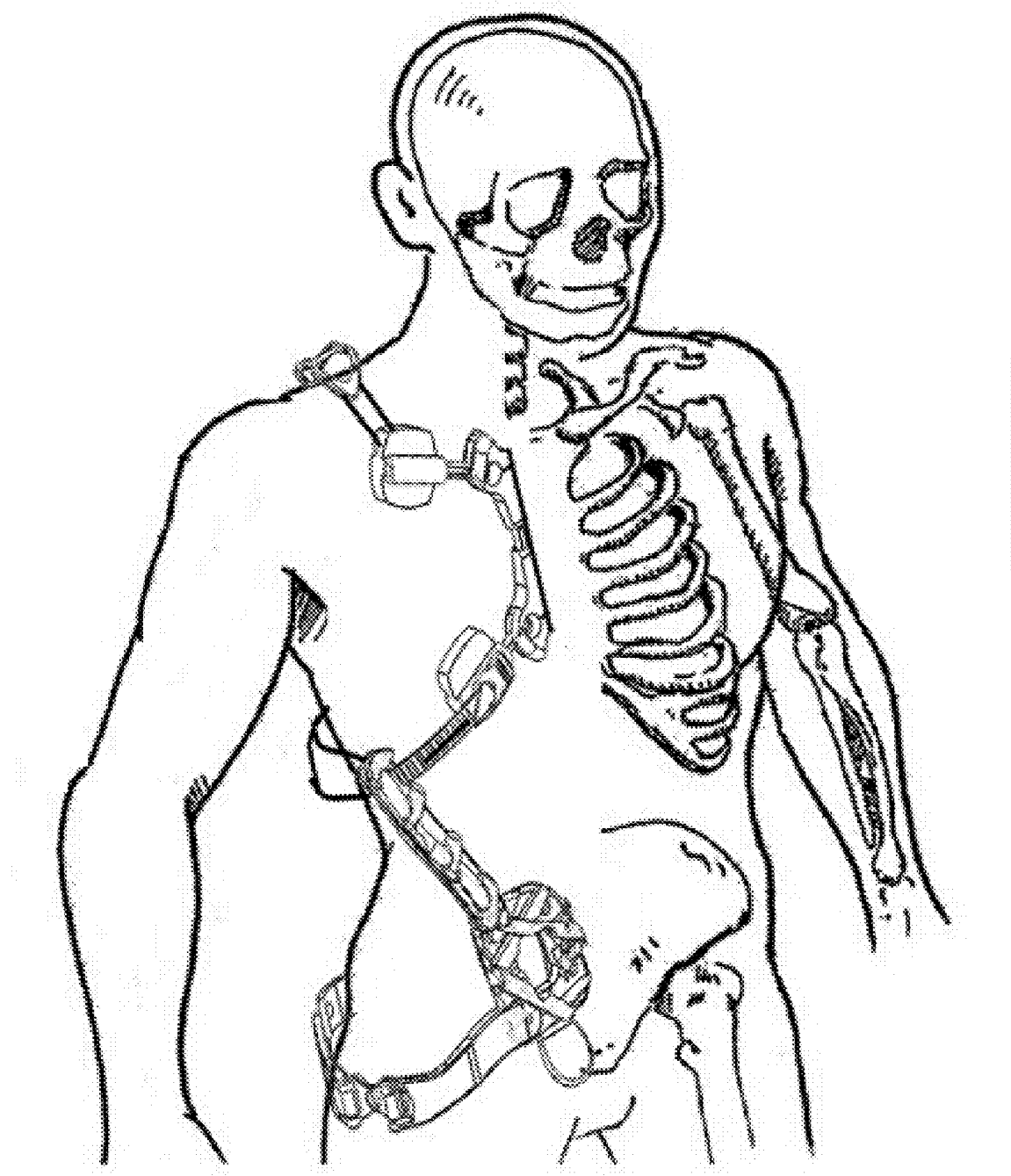
FIG. 2 is the Partial Anterior Perspective View Illustrating Anatomical Landmarks. This illustrates the underlying skeletal structure relative to the invention.

Selected embodiments of the present invention will now be explained with reference to the drawings. It will be apparent to those skilled in the art from this disclosure that the following descriptions of the embodiments of the present invention are provided for illustration only and not for the purpose of limiting the invention as defined by the appended claims and their equivalents.

This invention allows a variable mechanism which resists overloading, twisting and jerking, to isolate and protect the spine from sudden movement and painful loading of spine segments. The variable springs and tension components can also be used to inhibit motion to strengthen core muscles and provide therapy. The invention can be used to absorb loads, and transfer loads from upper extremity exoskeletons to lower extremity exoskeletons, and limit the loading and stresses on the spine. The core mechanical components of this invention constitute a spinal orthosis which can be considered to be a cervical thoracic scapular-thoracic lumbar sacral orthosis (CTSTLSO). The CTLSTO provides support, stability and/or immobilization of at least a portion of the vertebral column, which includes the cervical, thoracic, lumbar, sacral regions, following various traumatic injuries or surgical procedures, or during rigorous activity for example.

The variable torsional and spring joints and anatomically configurable sections, when connected to powered electro-mechanical components provide additional functional capacity and the invention can be used as a powered exoskeleton device. At each manually adjustable joint an electromechanical device with a control system can provide active control of the stiffness, or specifically provide control of and execution of the continuously variable torsional and linear spring stiffness. An electromechanical device with a control system can also provide control of and execution of the constantly variable joint angle at each of the locked joint sections. The invention can be worn intermittently or continuously by infirmed persons, or by healthy persons who are participating in rigorous activities.

It is an objective of the present invention to provide an inexpensive, reconfigurable, mass producible device (as compared to singly tailored orthoses) which enables spinal stabilization and controllable twisting, extension, flexion and bending motion of a trunk during static and dynamic activities. In accordance with the embodiment of the invention, the CTSTLSO includes an upper 49 and lower torso support 50 which is securable about the cervical, thoracic and lumbar sections of the wearer. The upper torso support 33 has an anterior assembly 34 which is connected to a posterior assembly 32 with two vertebral struts 51.

Sternal-clavicular assembly or crest 36 is connected to the posterior vertebral struts 26, 27 and to the lumbar assembly 38 via chondral 8, 19, 20, 37 and iliac digits 21, 22, 23, 39. The chondral 37 and iliac digits 39 are anterior-posterior assemblies that are connected to the vertebral struts 51. The size and geometry of sternal-clavicular crest 36 can be modified for comfort and for a secure fit on sternums and clavicles of multiple sizes.

The sternal-clavicular assembly 36 can be modified in length and the location angle of the arms or Clavicular digits 40, 41, 42, 44, 45, 46 can be altered and locked in position. The assembly has at least four arms 40, 41, 44, 45, 46, 47, 48 which have integrated rack-gear mechanism that allows the adjustment and locking of the anterior contact pads 45, 46 which rest on the clavicle. On the axis of the assembly 36 which is aligned with the axis of the manubrium of the sternum are two sternal pads 15, 16. The distance between the sternal pads can be varied. Varying the distance between the sternal-clavicular assembly pads 15, 16 can be done to contact the region of the xiphoid process for improved comfort and secure mechanical locking with the chondral digit 37, via a chondral stay 43. Angular positioning and locks are integrated within the sternal pads 15, 16 by circular rack and spur gear mechanisms. The two arms 44 that originate from the lower sternal pad 16 are chondral stays 47, 48 that connect to the chondral web 42 of the chondral digits 37.

An embodiment of the posterior assembly 6, 7, 8, 9, 10, 11, 12, 13, 25, 26, 27, 32 includes two longitudinal load bearing vertebral struts 51. These external scaffold struts provide support and correction to the alignment of the spine. The struts can be varied in geometry and length to conform to the length of the spine. The vertebral struts 51 are comprised of at least three sections 25, 26, 27 that correspond to the lumbar, thoracic and cervical sections of the torso. The angle of each section about the sagittal, longitudinal and the transverse axis can be independently varied. The angle can be adjusted to discretely conform to a preferred curvature of each section of the spinal column of a wearer. Adjustable linear and torsional springs and locks located at each vertebral boundary allow for varying the rigidity and range of motion of each section of the vertebral struts 51. The vertebral struts 51 incorporate a rack-gear mechanism 24 that allows the adjustment and locking of posterior contact pads. The posterior contact pads 9, 12 can be moved along the length of the vertebral struts 51 to provide support to the spinal column. The vertebral struts have at least one Lumbar Crossbar 10 and thoracic Crossbar 11 that connect and set the length between the struts 51.

An embodiment of the posterior assembly 6, 7, 8, 9, 10, 11, 12, 13, 25, 26, 27, 32 includes a cervical plate 13 at the cervical termination of the vertebral struts 51 and a sacral plate 6 at the sacral termination of the vertebral struts 51. The transverse angles of both plates can be set and adjusted, and torsional springs and locks located at each plate can limit the range of motion and the rotational stiffness of each plate.

An embodiment of the posterior assembly includes two cervical—scapular arms 12. Each arm is comprised of two anterior contact pads 7 and a scapular strut 52. An anterior pad 9 is connected to the cervical section of the vertebral strut 27. The scapular strut 52 is connected to the anterior contact 9 by a radial gear (or curvic) coupling mechanism that allows changing the angular position of the strut. The scapular struts 9 incorporate a rack-gear mechanism 24 that allows the adjustment and locking of scapula anterior contact pads 12. The scapula struts are of variable length and angular orientation. A variable stiffness spring and lock integrated within the cervical component 27 of the vertebral strut limits the range of motion and the rotational stiffness about the three axes of the scapula strut 52.

The scapula anterior contact pad 12 is connected to the sternal-clavicular assembly 36 by means of an adjustable shoulder strap 28 that is affixed to the Clavicular digit 40, 41,

42, 44, 45, 46. Adjustment of the strap can be performed to vary the strap orientation, location of padded strap sections and strap tension.

An embodiment of the posterior-anterior assembly includes a Posturo-lateral chondral digit 37 that originates at the thoracic section of vertebral struts 26 and terminates at the sternal-clavicular 36 assembly and at an abdominal Para-umbilical buttress 5 at the anterior section of the torso. There are a minimum of two digits, a left-hand and a right hand side digit. The chondral digit 37 is comprised of an anterior contact 9, an anterior chondral tensioner 18, a proximal 19 and distal phalange 20, and a chondral web 8 which is connected to the chondral stay 42 of the sternal-clavicular assembly 36. The chondral digit 36 runs along the intersection of the thoracic-lumbar region and partially rests on the lowest ribs of the torso. The position of the posterior contact can be moved along the vertebral strut 26. The anterior tensioner 18 and chondral web 8 can both be tightened and loosened as selected.

An embodiment of the posterior-anterior assembly includes a Posturo-lateral iliac digit that originates at the lumbar section of vertebral struts 25 and terminates at the abdominal Para-umbilical buttress 5 at the anterior section of the torso which the chondral digit 37 is also connected. There are a minimum of two digits, a left-hand and a right hand side digit. The iliac digit 39 is comprised of an anterior contact 9, an anterior iliac tensioner 18, a proximal 23, a medial 22 and distal phalange 21 which is connected to the abdominal Para-umbilical buttress 5. The iliac digit 39 runs along the intersection of the lumbar-sacral region of the torso and rests on the iliac crest. The section of the digit that is in the region of the iliac crest incorporates a gripping mechanism that allows for additional fixation to bony anatomy in this region. The position of the posterior contact can be moved along the vertebral strut 25. The anterior tensioner 18 can be loosened as selected. A torsional spring or gripping portion is located at medial iliac digit 22 is located at the connection between the anterior tensioner 23 and the proximal digit 21. The torsional spring can be adjusted to allow modifiable sagittal axis rotational stiffness of the phalanges of the iliac digits. A variable stiffness spring mechanism is integrated within the medial iliac digit to allow for varying the strength of the digit grasp.

Figure 3A:
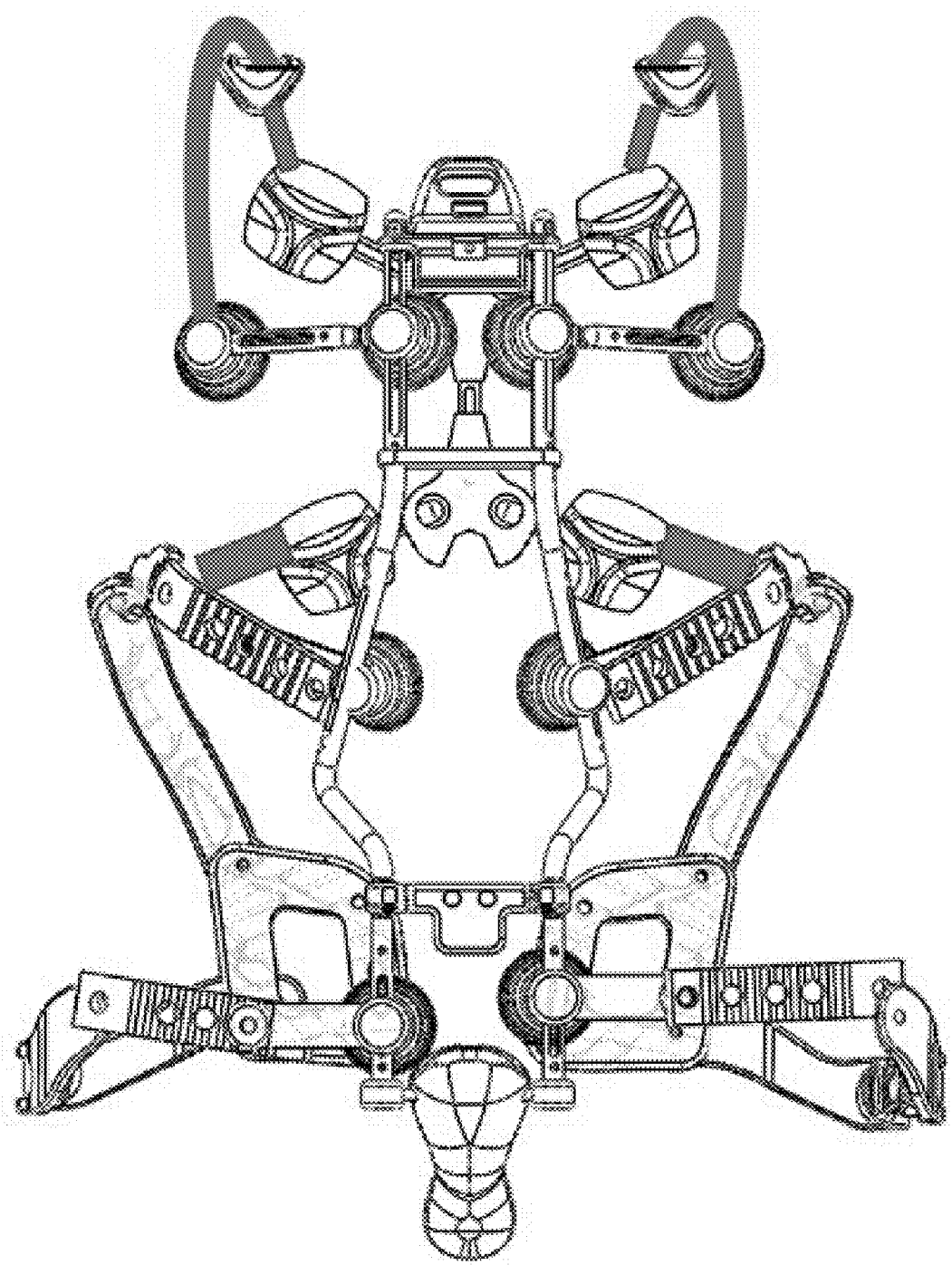
FIG. 3A is the Rear View, showing Anterior Scapular contact 7, the chondral digit anterior tensioner 8, the iliac digit anterior tensioner 9, the lumbar vertebral strut crossbar 10, the cervical strut crossbar 11, the Scapula strut 12, and the Cervical plate 13.
Figure 3B:
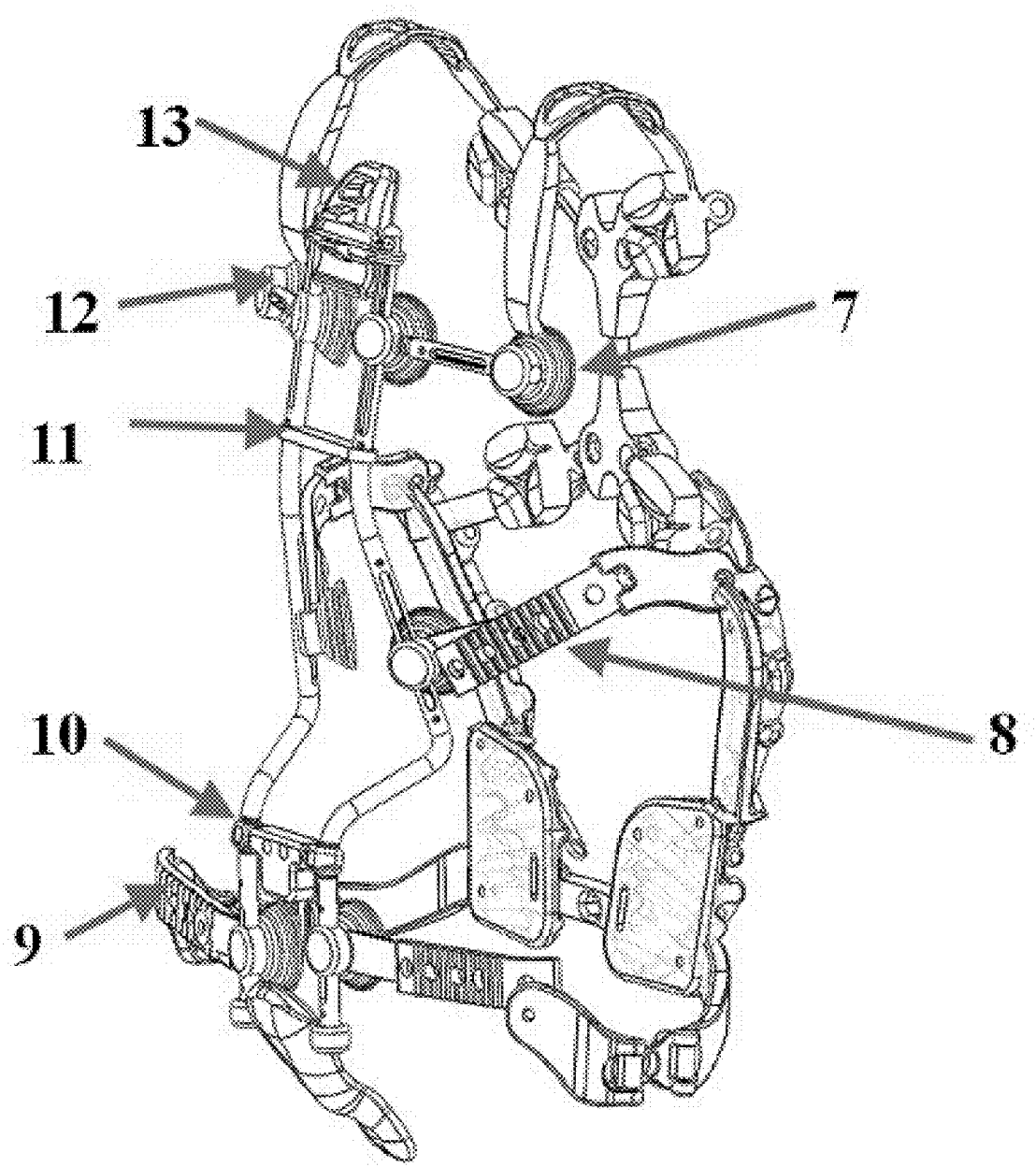
FIG. 3B is a side perspective view of the orthosis of FIG. 3A.
Figure 4:
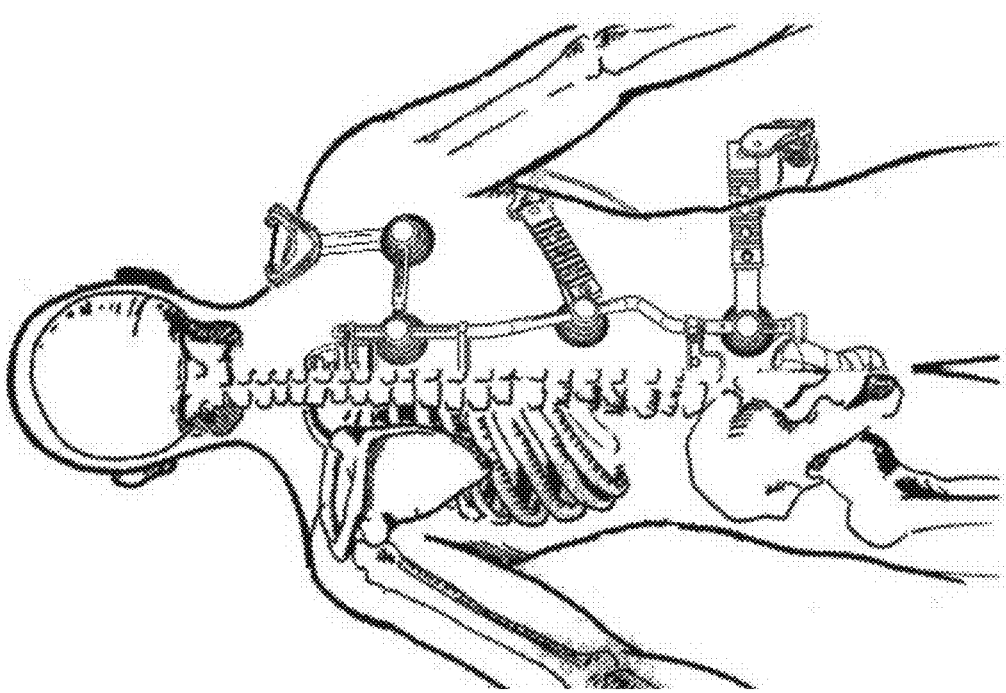
FIG. 4: Posterior Partial Projection Illustrating the anatomical Configuration
Figure 5:
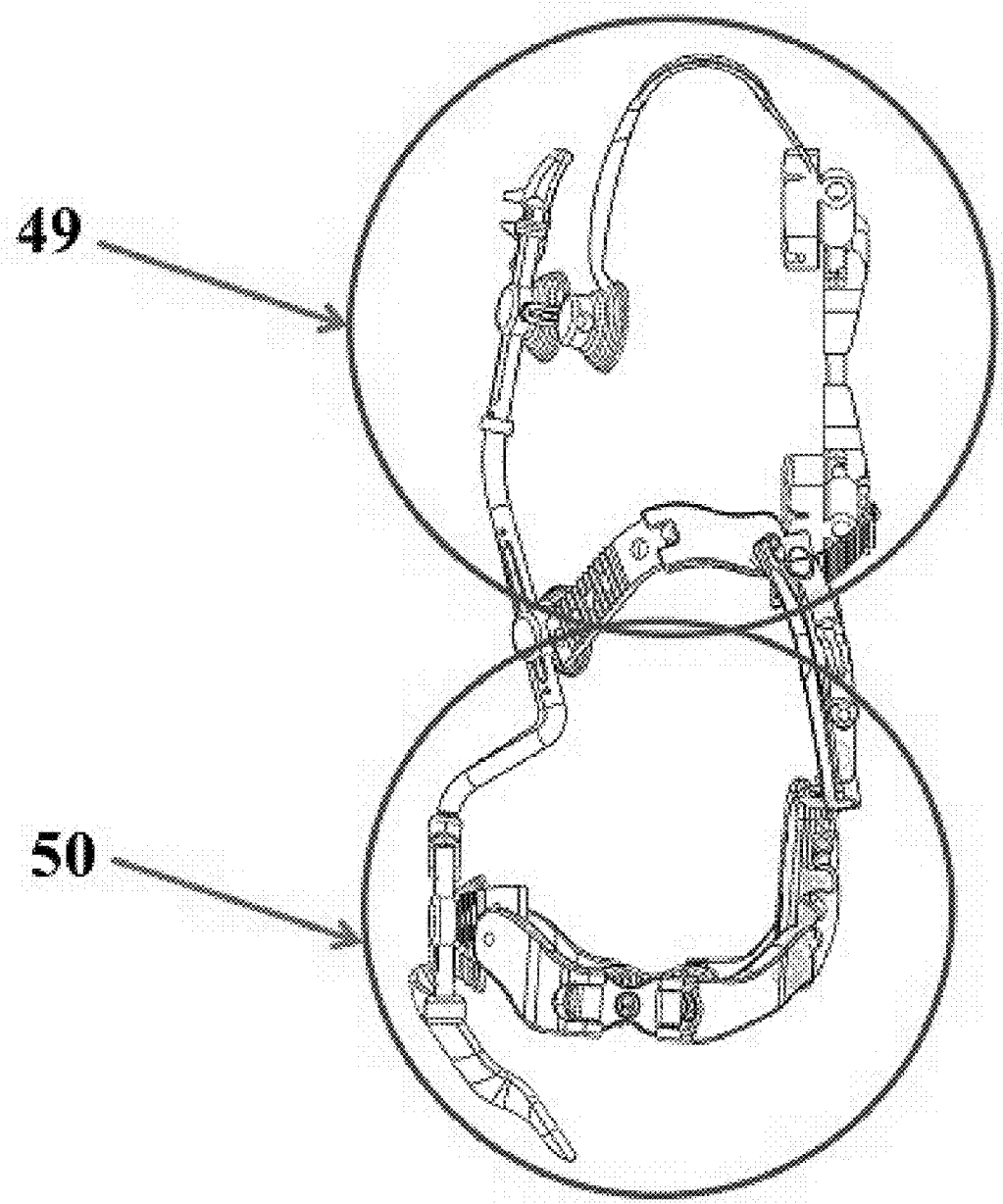
FIG. 5: Side View, the upper torso subassembly 49, and the lower torso sub-assembly 50.
Figure 6:
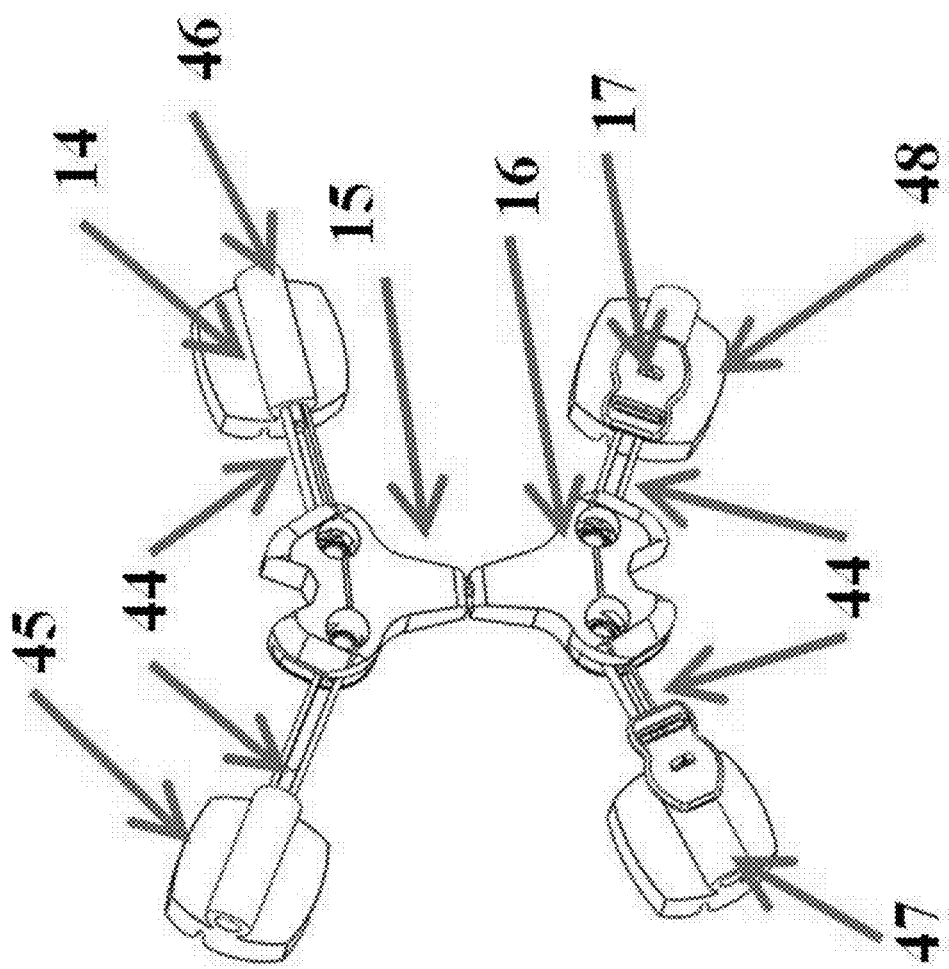
FIG. 6: Sternal-Clavicular Crest, showing the clavicle contact pad 14, the manubrium sternal pad 15, the xiphoid process sternal pad 16, and the Chondral stay tensioner 17.
Figure 7:
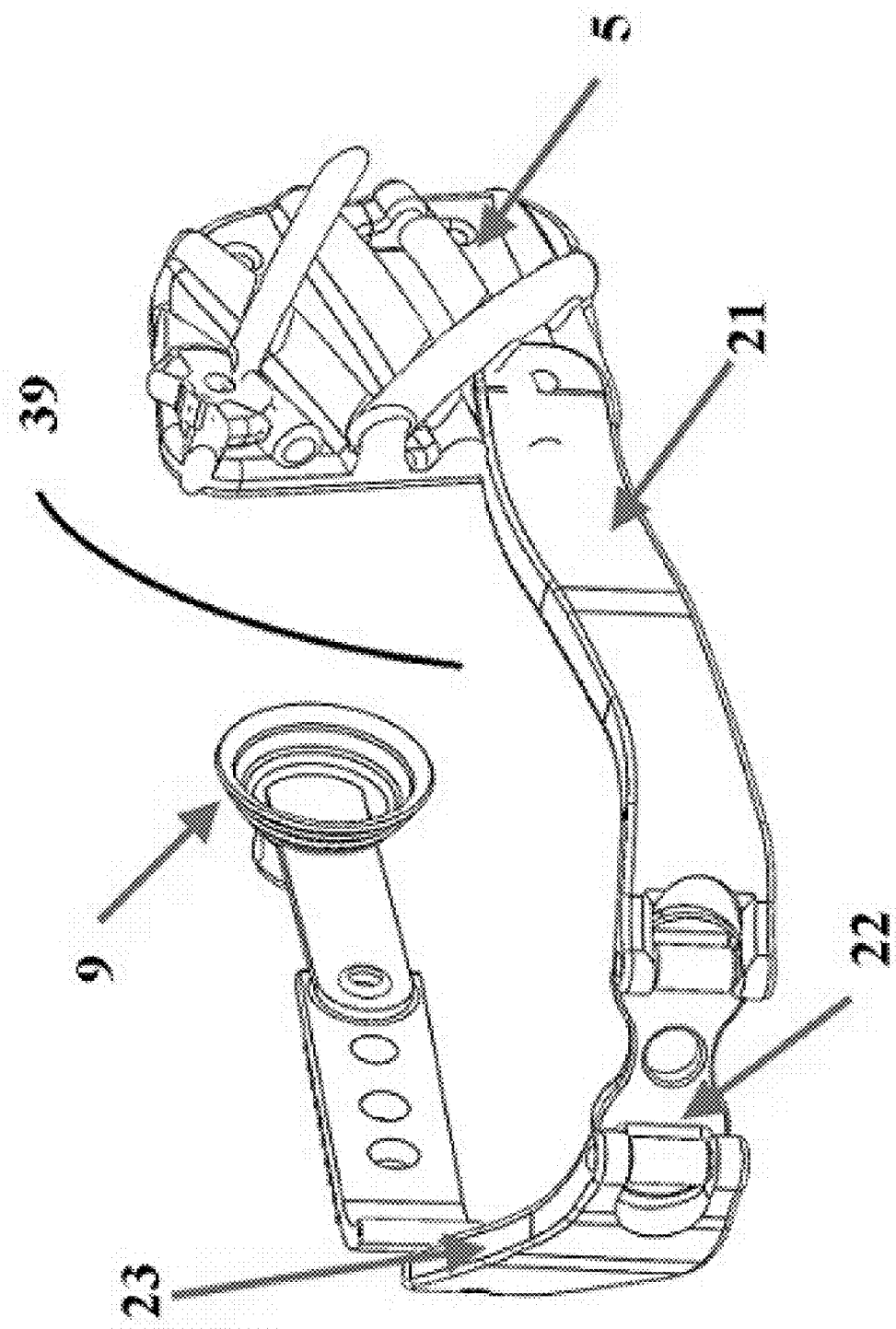
FIG. 7: Iliac Digit, showing the distal iliac digit 21, the medial iliac digit 22, and the proximal iliac digit 23.
Figure 8A:
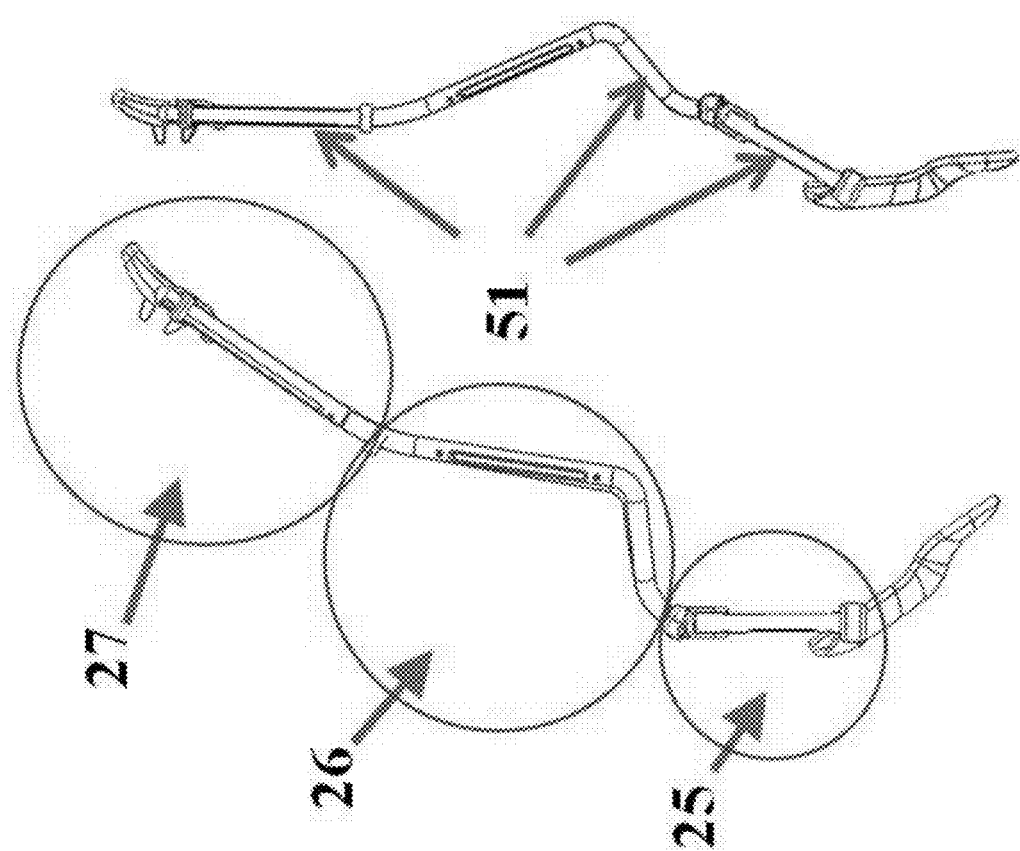
FIG. 8A: Vertebral Struts and Pelvic Plate Sub-Assembly, showing the three vertebral struts 51, the integrated gear rack component 24, the lumbar vertebral strut sub-assembly 25, thoracic vertebral strut sub-assembly 26, and the cervical vertebral strut sub-assembly 27.
Figure 8B:
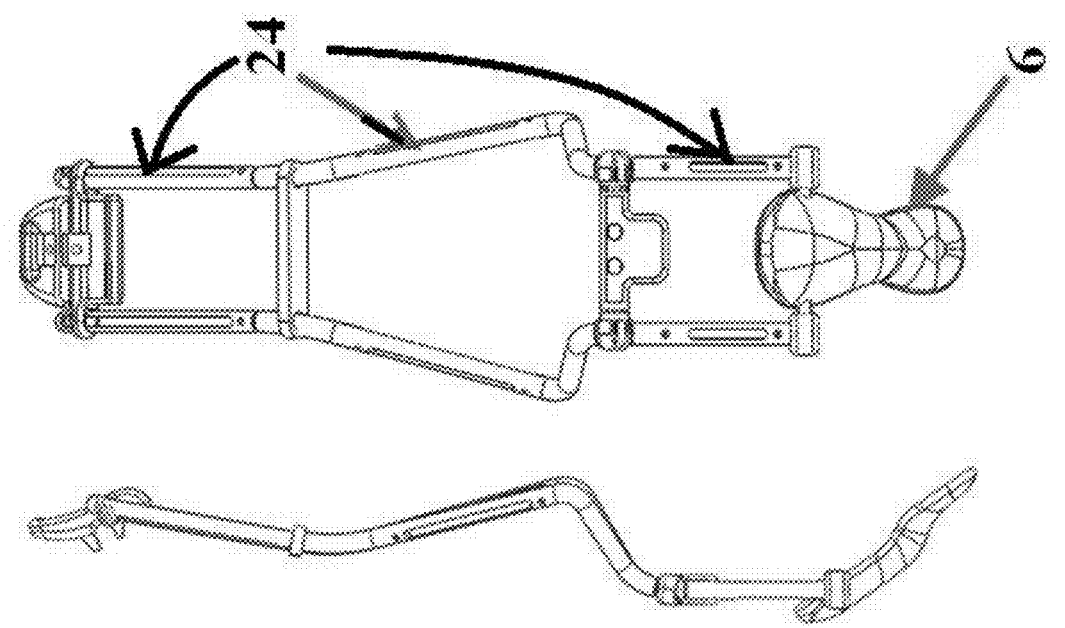
FIG. 8B is a side view of the sub-assembly of FIG. 8A.
Figure 9:
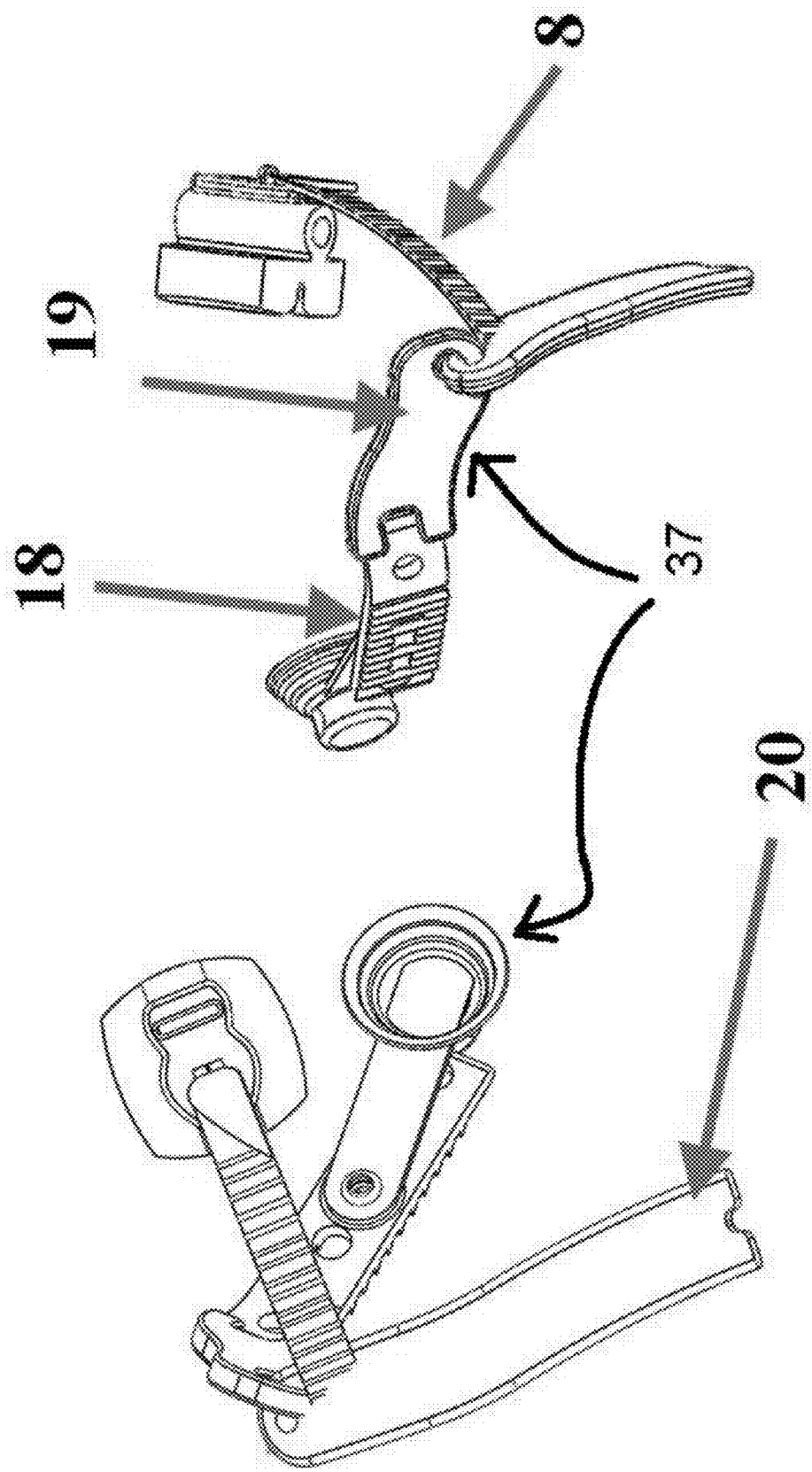
FIG. 9: Chondral Digit Front and Side Views, showing the chondral web 8, the chondral digit distal phalange 20, the chondral digit proximal phalange 19, and the chondral digit posterior tensioner 18.
Figure 10A:
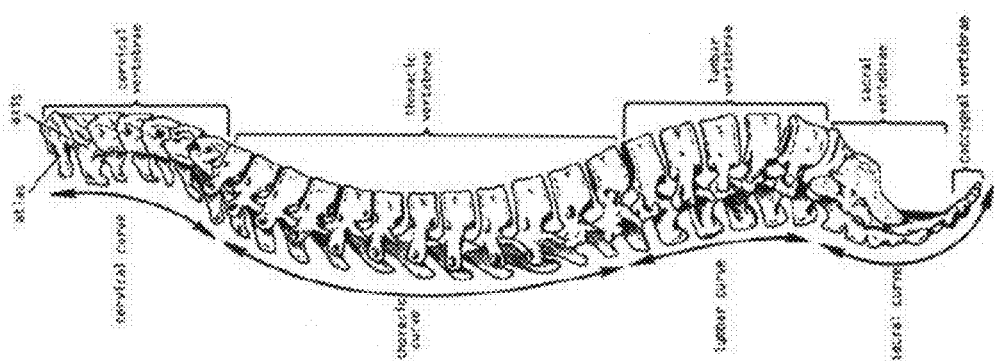
FIG. 10A: Curves and Segments of Human Spine
Figure 12:
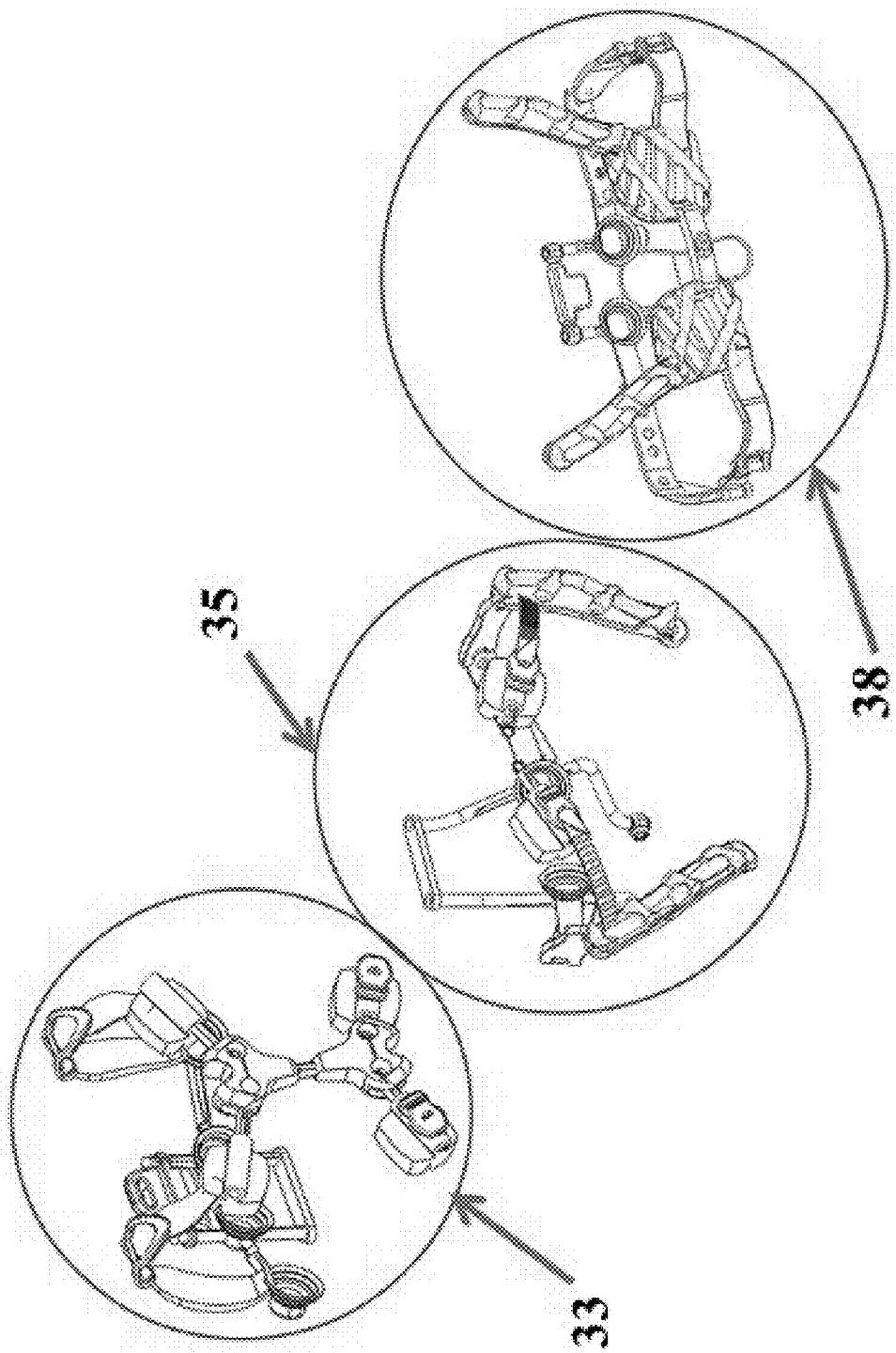
FIG. 12: Major Components (a) Cervical Sub-Assembly 33, (b) Thoracic Sub-Assembly 35, (c) Lumbar Sub-Assembly 38

An embodiment of the anterior assembly includes a minimum of two abdominal Para-umbilical buttresses 5, a left-hand and a right hand side buttress. The Para-umbilical buttresses 5 may be constructed with internal supports, visible in FIGS. 1A, 1B, 2, 7, and 12, and obscured in FIGS. 3A and 3B. These are connected to each other by an adjustable strap 53. The overall embodiment may be constructed in certain limited sizes to accommodate different sized trunks. The anterior assemblies and posterior assemblies may be mixed and matched in various combinations to fit the physical dimensions of virtually any person. The interchangeable parts will accommodate a wide range of limb geometries, overall sizes and lengths. Embodiments of the present invention minimize the need for time and resource-intensive customized fitting and create an affordable, relatively low-cost orthosis.

The invention provides postural support by means of vertebral struts 51 which incorporate a rack gear mechanism 24 that allows adjustability and locking on the torsos of multiple individuals extending from the sacral to cervical sections of the spine. The invention provides an apparatus for the active strengthening of weak postural and phasic muscles by the use of anatomically configurable components that incorporates multiple variable torsional and linear springs that encapsulate and grasp the torso. The invention provides variable resistance to motion of the spine in anterior posterior planes.

The invention provides an apparatus for posture correction, and external vertebral column and an external support on the ribs, reduces the amount of core effort required to maintain upright posture. The invention enables more control of the core through a flexible articulated structure. The angle of the Veterbral Struts 51 and Sacral Plate 6 can be adjusted to maintain the curvature of the lumbar—cervical and the thoracic region. The tension at the joints at each section of the struts can be varied to prohibit movement or overextension of spinal sections. A combination of posterior and anterior gripping components and the located rigid components of the exoskeletal structure supports the spine and provide upright postural stability. This reduces the weight experienced on thoraco-lumbar section of the spine. The invention promotes an upright posture by stabilizing the Coccyx and the Pelvis, preventing sway of the vertebral column and reducing gross trunk motion. In this embodiment of the invention self-mobilization of the cervical and thoracic spine provided. The preferred embodiment assembly provides abdominal support to those with weakened core strength and augments what the abdominal core does. The invention provides an apparatus for trunk support, core strengthening and for core stabilization.

The invention is to provide a wearable lightweight device. Particularly, the invention achieves a skeletal garment for wearing about the lower, mid and upper torso, the garment allows the lifting of the wearer by connecting to multiple sections along the posterior of the exoskeleton. The embodiment of the invention provides a spinal orthosis device which includes an anterior and posterior, medial and lateral, abdominal opening, and a continuous frame. In the preferred embodiment the iliac digits forms a ring around the top rim of the pelvis and articulates with the sacral plate 6, providing stabilization about the lumbar-sacral spine. Varying the tension at the iliac digit 39 allows running strength training when hip tilt is required. Chondral 37 and iliac digits 39 both connect to an abdominal para-umbilical buttress 5. Combined effect is to provide a secure mechanical lock about the trunk. The strength of the lock can be adjusted as desired by varying the adjustable torsional springs and or the anterior and posterior tensioners. The varied tensioning can limit the potential of the spine slipping to one side and reduces the tendency of scholiotic curvature, or neuromuscular imbalance to prevent slipping of the thorax and taking the spine out of alignment. The preferred embodiment provides lateral stabilization at the upper thorax which is supported by contacts at the trapezius and the scapula level 7, 12, also fixating the device on the ischial spine to provide lower support. The Chondral web 42 can be used to strengthen diaphragmatic breathing. The tension of the section provides a method to increase the constraint on the lung to force strengthening the lung cavity and Lung capacity. When correctly tensioned the device increases the use in the accessory muscles of breathing: between the rectus abdominus and the lateral obliques around the abdomen there will need to increase their stabilizing force.

In a preferred embodiment, the tensioned chondral digit 37 can reduce the amount of movement at the rib level inducing more inspiration due to abdominal breathing. At the level of the lower lobes of the lungs there will be reduced lateral expansion, which will encourage compensatory effort by the user which will result in increased inferior expansion into the abdominal cavity during inspiration.

The invention places the pelvis into an anterior tilt in combination with stabilizing the scapula and the trunk, this mechanically limits spinal Hyperextension. The invention provides an orthosis with a structure that allows modification of flexion and extension through variable springs and elastic components. Using adjustable tension springs, and elastic sections which can be configured to the dimensions and anatomy of the wearer, various and variable sizes and shapes for the spinal orthotic device are enabled. In the preferred embodiment the invention will stabilize the spine and will require less cognitive focus by the wearer to control gross truncal motion. A plurality of adjustment straps on a chondral digit allows tensioning of the digit to allow a secure grasp of the trunk. The device can be tuned to provide corrective postural and motion support to individuals during multiple activities.

Variable torsional springs located at the iliac and chondral digits, vertebral struts, pelvic and cervical plates can be used to inhibit unsteady motion, to limit extension of spinal sections, to provide resistance for exercise and strengthening. The anterior contact pads are comprised on cushioning and linear springs which can be tuned to provide variable resistance to motion of the spine. Anterior contact pads protect from impact and shock loading The lumbar-sacral 6, 51 sections can be connected to assorted external structures to transfer load from the body completely.

In the preferred embodiment the scapula sections prevent winging of the scapula 7, 12, 28. This sub-assembly provides a depressing force on the elevated scapula. This provides a variable reaction force scapular motion. The preferred embodiment supports the recruitment of motor units for control, by reducing the demand on the musculature to support the segments of the torso and allowing more capacity to be focused on control. External struts 51 allow core muscles to focus on control, relieving load on Vertebral column. The embodiment relieves compression on abdominal organs, relieves bladder pressure and may relieve difficulties of how the bladder functions without the continuous pressure. Thoracic pads 7, 55 reduce scoliotic curves and maintain curve reduction for the duration of wear, by imposing constraints on the first thoracic vertebra. The invention further provides correction and stability of primary thoracic curves, axillary sling forces must be considered in addition to the thoracic and lumbar pad force. The adjustable tensioners 8, 9, 28, 42 and digits 37, 39 can be used to create alignment of the spine, while aiding in gradually stretching and lengthening the spine. The combined effects of endpoint control, curve correction and continuous lateral support in orthotic stabilization, can reduce the effects of skeletal changes from long standing neuromuscular instability, by relieving the spine and hence allow the development of increased neuromuscular strength in control in the wearer.

In the preferred embodiment the digits are comprised of a chain of removable and extendable linkages that can be angularly adjusted. The linking digits create a bridge and/or connect the posterior struts to the anterior components. These components allow adjustability for different sized torsos. The stiffness of joints connecting each digit can be altered to lock or have varying degrees of compliance.

In understanding the scope of the present invention, the term "configured" as used herein to describe a component, section or part of a device includes hardware and/or software that is constructed and/or programmed to carry out the desired function. In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A spinal orthosis comprising:
   a cervical section having one or more pads configured for placement at a clavicle of a wearer;
   a lumbar section connected to the cervical section and having an abdominal para-umbilical buttress configured for an anterior region of a lumbar spine, the buttress being further configured to provide compression and gripping of the spine, the lumber section including one or more digits with a gripping portion at around ribs and/or iliac crest of the wearer;
   a thoracic section connected to the cervical section;
   a tensioner connecting the lumbar section to the thoracic section; and
   wherein the buttress includes metal wire in patterns.

2. The spinal orthosis of claim 1, wherein the wire includes braided fiber.

3. The spinal orthosis of claim 1, wherein the pattern is woven and/or wound.

4. The spinal orthosis of claim 1, wherein the pattern is a honeycomb pattern.

5. The spinal orthosis of claim 1, wherein the tensioner is attached to the digit to provide positioning and compression of the abdomen.

6. The spinal orthosis of claim 1, further comprising an electromechanical device with a control system configured to execute variable torsional and linear spring stiffness of the tensioner.

7. The spinal orthosis of claim 1, further comprising an electromechanical device with a control system configured to execute variable joint angles.

8. The spinal orthosis of claim 1, further comprising one or more struts connected to the digit, the strut being configured to provide support to a spinal column of the wearer.

9. The spinal orthosis of claim 1, further comprising a segmented elastic pelvic plate that conforms to the sacrum with varied degrees of stiffness frigidity, an angle of the pelvic plate being variable relative to the lumbar section of the orthosis.

10. The spinal orthosis of claim 1, further comprising a sacral spine segment and a plurality of connectors at an intersection of each lumbar, thoracic, cervical and sacral spine segments that integrate multiple variable stiffness linear and torsional joints that correspond to each axis of the spine.

11. The spinal orthosis of claim 1, wherein the lumbar, thoracic and/or the cervical sections can be used to manually or by means of a control system modulate inspiratory effort/motion and patterns through a combination limiting rib excursion by variably tensioning the chondral digit and the abdominal buttress/sheath, thereby causing effort required to perform diaphragmatic breathing and tension applied at the inferior border of the rib margin will alter lateral excursion of the lower ribs and further altering the load on a cardio-vascular system of the user.

12. The spinal orthosis of claim 11, wherein arterial resistance is modified as a result of pressure on the large abdominal vessel.

13. The spinal orthosis of claim 12, wherein a cardiovascular benefit is provided by releasing the cardiac load the resistance to output and increasing the venous return to modify cardiovascular performance, thereby modulation of the inspiratory system can be used to support healthy breathing and increase breathing difficulty for rehabilitation.

14. A spinal orthosis comprising:
a cervical section having one or more pads configured for placement at a clavicle of a wearer;
a lumbar section connected to the cervical section and having an abdominal para-umbilical buttress configured for an anterior region of a lumbar spine, the buttress being further configured to provide compression and gripping of the spine, the lumber section including one or more digits with a gripping portion at around ribs and/or iliac crest of the wearer;
a thoracic section connected to the cervical section;
a tensioner connecting the lumbar section to the thoracic section; and
integrated electro-mechanical digits and joints that allow dexterous manipulation of the spine during stationary and dynamic locomotion activities, thereby providing a modular and adjustable end-effector or gripper that can be used to grasp and manipulate the spine of a wearer.

15. The spinal orthosis of claim 14, wherein the joints are adjustable to lock to vary the linear, angular and torsional stiffness for grasping torsos of different sizes and shapes in many gripping patterns.

16. The spinal orthosis of claim 15, wherein a strength of the grasp can be altered by rigidly locking the digits, and/or by tensioning elastic straps that pull on segments of the digit.

17. A spinal orthosis comprising:
a cervical section having one or more pads configured for placement at a clavicle of a wearer;
a lumbar section connected to the cervical section and having an abdominal para-umbilical buttress configured for an anterior region of a lumbar spine, the buttress being further configured to provide compression and gripping of the spine, the lumber section including one or more digits with a gripping portion at around ribs and/or iliac crest of the wearer;
a thoracic section connected to the cervical section;
a tensioner connecting the lumbar section to the thoracic section; and
wherein the buttress includes a split helically wound tube embedded within a rubber or flexible elastic sections.

18. A spinal orthosis comprising:
a cervical section having one or more pads configured for placement at a clavicle of a wearer;
a lumbar section connected to the cervical section and having an abdominal para-umbilical buttress configured for an anterior region of a lumbar spine, the buttress being further configured to provide compression and gripping of the spine, the lumber section including one or more digits with a gripping portion at around ribs and/or iliac crest of the wearer;
a thoracic section connected to the cervical section;
a tensioner connecting the lumbar section to the thoracic section; and
an electromechanical device with a control system configured to control stiffness of the tensioner.

* * * * *